(12) United States Patent
Fishburne, Jr.

(10) Patent No.: US 10,912,540 B2
(45) Date of Patent: *Feb. 9, 2021

(54) BODILY FLUID INDICATOR DEVICES AND METHODS

(71) Applicant: FISHBURNE MAY, LLC, Rock Hill, SC (US)

(72) Inventor: Coty Fishburne, Jr., Rock Hill, SC (US)

(73) Assignee: FISHBURNE MAY, LLC, Rock Hill, SC (US)

( * ) Notice: Subject to any disclaimer, the term of this patent is extended or adjusted under 35 U.S.C. 154(b) by 297 days.

This patent is subject to a terminal disclaimer.

(21) Appl. No.: 16/050,531

(22) Filed: Jul. 31, 2018

(65) Prior Publication Data

US 2018/0333143 A1  Nov. 22, 2018

Related U.S. Application Data

(63) Continuation of application No. 15/439,134, filed on Feb. 22, 2017, now Pat. No. 10,058,307.

(60) Provisional application No. 62/395,683, filed on Sep. 16, 2016, provisional application No. 62/298,561, filed on Feb. 23, 2016.

(51) Int. Cl.
| | |
|---|---|
| A61B 5/00 | (2006.01) |
| A61B 10/00 | (2006.01) |
| A61B 5/145 | (2006.01) |
| A61B 5/1473 | (2006.01) |
| A61B 5/01 | (2006.01) |

(52) U.S. Cl.
CPC ........ *A61B 10/0051* (2013.01); *A61B 5/1473* (2013.01); *A61B 5/14507* (2013.01); *A61B 5/14539* (2013.01); *A61B 5/4261* (2013.01); *A61B 5/01* (2013.01); *A61B 5/14517* (2013.01); *A61B 5/14546* (2013.01); *A61B 5/4266* (2013.01); *A61B 5/4288* (2013.01); *A61B 5/4294* (2013.01); *A61B 2010/0003* (2013.01); *A61B 2010/0006* (2013.01); *A61B 2010/0074* (2013.01); *A61B 2562/0295* (2013.01)

(58) Field of Classification Search
None
See application file for complete search history.

(56) References Cited

U.S. PATENT DOCUMENTS

| | | | |
|---|---|---|---|
| 5,135,005 A * | 8/1992 | Nagase | A61B 3/101 600/573 |
| 9,297,724 B2 * | 3/2016 | Chen | G01N 1/10 |

(Continued)

*Primary Examiner* — Christian Jang
*Assistant Examiner* — Sarah R Kingsley
(74) *Attorney, Agent, or Firm* — E. Eric Mills; Nexsen Pruet, PLLC (57) ABSTRACT

Bodily fluid indicator devices and methods are provided. Such devices and methods can effectively indicate whether the amount of bodily fluid being produced is within a measurable range. In an exemplary embodiment, a bodily fluid indicator device includes a substrate having a surface. Some portions of the surface are covered with a region of absorbent material and other portions of the surface are devoid of the absorbent material. A graduated scale or a reactive feature is printed on the absorbent material. The device is configured to indicate an amount and/or a composition a bodily fluid present on an area of a patient or subject.

13 Claims, 4 Drawing Sheets

(56) References Cited

U.S. PATENT DOCUMENTS

| | | | |
|---|---|---|---|
| 10,058,307 B2* | 8/2018 | Fishburne, Jr. | A61B 10/0051 |
| 2005/0147537 A1* | 7/2005 | Sangha | C12Q 1/6806 |
| | | | 422/550 |

* cited by examiner

BODILY FLUID INDICATOR DEVICES AND METHODS

CROSS REFERENCE TO RELATED APPLICATIONS

This patent application is a continuation of U.S. patent application Ser. No. 15/439,134, filed Feb. 22, 2017, which claims the priority benefit under 35 U.S.C. § 119(e) of U.S. Provisional Patent Application No. 62/298,561 filed on Feb. 23, 2016, and U.S. Provisional Patent Application No. 62/395,683, filed on Sep. 16, 2016, the contents of each of which are herein incorporated by reference in their entirety.

FIELD

The present invention relates to devices for obtaining bodily fluid and, in particular, to bodily fluid indicator devices and methods for indicating various attributes associated with bodily fluid.

BACKGROUND

The human body produces and secretes various bodily fluids, including, but not limited to saliva, sweat, nasal fluid, vaginal fluid, etc. Changes in the amount of a bodily fluid being produced and/or changes in the composition of the bodily fluid being produced can be indicators of a subject's overall health. For example, a shortage or overage in production of some types of bodily fluids can be indicative of disease or a health concern, such as the existence of a tumor, an autoimmune disease, or diabetes, just to name a few.

Currently, tests that indicate the amount and/or composition of bodily fluid being produced are determined using measures of fluid (e.g., saliva is removed from the mouth and then measured). Existing tests are also performed over a period of several minutes, typically five minutes or longer. The prolonged length of these tests can be uncomfortable to the subject.

Accordingly, a need exists for improved bodily fluid indicator devices and methods, which can effectively indicate whether the amount of bodily fluid being produced is within a measurable range.

SUMMARY

Bodily fluid indicator devices and methods are provided and disclosed herein. In an exemplary embodiment, a bodily fluid indicator device is provided. The device comprises a surface and a graduated scale or reactive feature. Some portions of the surface are covered with a region of absorbent material and other portions of the surface are devoid of the absorbent material. The graduated scale or reactive feature is printed on the absorbent material. The graduated scale can be printed using a U.S. Food and Drug Agency (FDA) approved ink, including but not limited to a food grade ink.

In further embodiments, the substrate is flexible. The substrate may comprise an organic or inorganic material. The substrate can comprise paper and be planar or curved. Moreover, device can comprise a plurality of bendable tabs that extend from the surface. The tabs are configured to rest against a portion of a subject's body during a bodily fluid measurement.

Additionally, the substrate can comprise a body portion and a stem portion extending from the body portion. The body portion can be at least 0.5 inches wide and the stem portion can be at least 0.125 inches wide. Notably, the devices set forth herein are configured to indicate an amount and/or a composition a bodily fluid present on an area of a patient or subject. The bodily fluid can comprise saliva, sweat, nasal fluid, breast milk, breast discharge, or vaginal fluid.

In a further aspect, a method of using a bodily fluid indicator device is provided. The method can comprise providing a bodily fluid indicator device comprising a region of absorbent material and a graduated scale printed thereon. The method can further comprise contacting a bodily fluid with the indicator device for a period of time sufficient to cause the bodily fluid to migrate over a portion of the graduated scale, wherein the period of time is less than one minute. The method can further comprise determining a measurable amount of bodily fluid being produced based on a proportion of the graduated scale over which the bodily fluid has migrated.

In yet a further aspect, an additional method of using a bodily fluid indicator device is provided. The method comprises providing a bodily fluid indicator device comprising a region of absorbent material and one or more reactive features printed thereon and contacting a bodily fluid with the indicator device for a period of time sufficient to cause the bodily fluid to migrate over a portion of the one or more reactive features. The period of time is less than one minute. The method can further comprise indicating an absence or presence of a chemical constituent forming the bodily fluid based on a reaction of the one or more reactive features over which the bodily fluid has migrated. The reaction can comprise a change in color, intensity, visibility, size, and/or shape of the one or more reactive features.

These and other embodiments are described in more detail in the detailed description which follows.

DETAILED DESCRIPTION

Bodily fluid indicator devices and methods are described herein which may provide one or more advantages over prior devices. Bodily fluid devices and methods herein are configured to indicate whether the type and/or amount of bodily fluid being produced is measurable. Bodily fluid devices and methods herein are also configured to indicate other attributes associated with a bodily fluid, such as attributes relating to composition (e.g., specific elements or chemical present, whether a yeast or bacteria are present, whether a hormone is present, etc.), temperature, or pH. Notably, devices and methods described provide quicker and/or more easily readable results than prior devices.

For example, the devices and methods herein are configured to test bodily fluid via a bodily fluid indicating device to indicate whether the chemical composition and/or amount of bodily fluid is within an accepted range, and the test can be performed in less than one minute.

Moreover, devices and/or methods described herein can be easily obtained and/or used by any health care provider (e.g., dentist, physician, nurse, pharmacist, etc.) or a subject, either in a clinical setting, a pharmacy setting, or in a home-use environment (i.e., a self-test). The self-test can be performed over a short course of time for an indication of whether the bodily fluid production is increasing or decreasing.

I. Bodily Fluid Indicator Devices

In some aspects, devices for indicating the type and/or amount of bodily fluid being produced are provided. In some embodiments, devices herein comprise a substrate. The substrate can be rigid, semi-rigid, or flexible. In some embodiments, the device comprises a thin device having a thin substrate, the device being configured for insertion within and/or contacting a subject's body (e.g., a mouth, eye, or nipple) to indicate an amount of bodily fluid present, a pH or temperature of the fluid, a composition forming the bodily fluid, and/or compositional elements (e.g., chemicals, bacterial, hormones, yeast, etc.) present or absent in the bodily fluid. In some embodiments, the device comprises a multi-dimensional solid or hollow device configured for insertion within the subject's body (e.g., a vagina or nose) for indicating an amount of bodily fluid present and/or a composition forming the bodily fluid.

The device substrate can comprise at least one surface that faces a source of the bodily fluid (e.g., a tongue, a vaginal wall, a nasal cavity, etc.). Some portions of the surface can be covered with a region or area of absorbent material and other portions of the surface can be devoid of the absorbent material. The absorbent material can comprise a porous material, a fibrous material, a porous paper, a filter paper, an absorbent paper, a woven or non-woven material, etc. Bodily fluids can advance or migrate from the fluid source (e.g., a tongue, vaginal wall, etc., or portion thereof), which contacts a proximal end of the absorbent material, towards a distal end of the absorbent material. The distal end of the absorbent material can be disposed outside of the subject's body. Thus, the fluid can migrate via capillary or osmotic action from one end of the absorbent material that is inside the subject's body towards a second end of the absorbent material that is outside of the subject's body, for example, where a graduated scale or one or more features are printed.

In certain embodiments, the substrate can comprise or be formed from a polymeric material such as a polystyrene (PS) (e.g. 0.01 polystyrene, 0.03 polystyrene, or 0.04 polystyrene). However, it is to be understood that the substrate is not limited to a polystyrene. Other materials may include polymeric materials, organic materials, plastic, polyethylene terephthalate (PET), polyethylene (PE), high-density polyethylene (HDPE), polyvinylidene chloride (PVDC), polypropylene (PP), high impact polystyrene (HIPS), polyamide (PA), and/or polycarbonate (PC). Non-plastic materials may also be used. In some embodiments, the substrate comprises or is formed from a food approved or food safe material, and/or comprises or is formed from a material which minimizes or reduces the risk of injury to the subject's mouth, gums, and/or teeth.

The substrate can have any dimensions or shape not inconsistent with the objectives of the present invention. For example, in some embodiments, the substrate is square, rectangular, and/or comprises one or more curved sections. Such shapes may be adapted as a "one size fits all" shape or size so that subjects of most or all ages or sizes may use the devices without modification. In addition, the substrate's size and/or shape may accommodate a subject with all of his or her teeth, some of his or her teeth missing, or with no teeth.

In some embodiments, a graduated scale and/or one or more reactive features may be printed on or over the absorbent material. The phrase "reactive feature" refers to a feature printed on the test device that has a chemical composition which is reactive to the presence or absence of a chemical, bacteria, yeast, temperature, pH, or a specific Biomarker. The chemical composition may react by changing color, intensity, size, shape, visibility, etc., in reaction to detecting the presence or absence of the chemical, bacteria, yeast, etc. For example and in some embodiments, where specific bacteria are present in the bodily fluid and a reactive feature which targets the specific bacteria is printed on the device, the feature may appear (i.e., become visible), change color, size, intensity, etc., to indicate that the specific bacteria are present.

The graduated scale and/or other features printed on or over the absorbent material can be printed from a U.S. Food and Drug Agency (FDA) approved ink, such as a water soluble food grade ink, a plant based dye or stain, an edible material, etc. Any U.S. FDA approved ink may be used that is not inconsistent with the objectives of the present invention. Exemplary FDA approved inks may include FDA approved toner inks that are non-toxic to humans and FDA 21 C.F.R. compliant. The graduated scale and/or other features can indicate an amount and/or a chemical composition of a bodily fluid, including, but not limited to fluids such as saliva, nasal fluid, breast milk, breast discharge, or vaginal fluid. As noted above, the presence or absence of a chemical or elemental constituent or composition, hormone, etc. may also be determined via one or more reactive features printed on or over the absorbent material.

In some embodiments, the substrate comprises a flexible substrate. In other embodiments, the substrate comprises a rigid or semi-rigid substrate. The substrate may be organic or inorganic. In some embodiments, the substrate comprises paper. In other embodiments, the substrate comprises plastic. The substrate can be solid or porous. The substrate can comprise any material that is not inconsistent with the objectives of the instant disclosure.

In some embodiments, the substrate is two-dimensional. In other embodiments, the substrate is three-dimensional. In some embodiments, the substrate has a square, circular, or rectangular sectional shape. The substrate may be planar, non-planar, rounded, angled, or curved. Any size and/or shape of substrate can be provided, so long that it is not inconsistent with the objectives of the instant disclosure.

In some embodiments, the substrate comprises a body portion and a stem portion. A plurality of bendable tabs can extend from portions of the substrate. The tabs are configured to prevent a portion of the device from extending into a body or orifice of a subject and/or prevent a portion of the device from contacting the bodily fluid. For example, in some embodiments, the tabs prevent the stem portion from extending into portions of the subject's body (e.g., the nose, mouth, vagina, etc., of the subject). The tabs are also helpful for elevating the substrate on a flat surface for obtaining easier readings.

In some embodiments, the substrate comprises or is formed from a food approved or food safe material, and/or comprises or is formed from a material which minimizes or reduces the risk of injury to the patient's body.

In some embodiments, the absorbent material is attached to the substrate. For example, the absorbent material may be laminated to the substrate. In some embodiments, the absorbent material is applied via mechanical clamping or heat. Other attachment methods are contemplated.

The substrate can have any dimensions or shape not inconsistent with the objectives of the present invention. For example, in some embodiments, one or more portions of the substrate can be square, rectangular, rounded, elongated, and/or comprise one or more curved sections. Such shapes may be provided in a "one size fits all" shape or size and/or optionally adapted from the "one size fits all" shape or size to a customized size or shape so that subjects of most or all ages and/or sizes may use the devices described herein without modification.

Bodily fluid indicator devices described herein may optionally be provided in a kit. For example, such devices may be provided in kits for use in the measurement of saliva production. Such kits, in some embodiments, comprise a plurality of saliva test members and a display rack. The test members can each comprise a rigid or semi-rigid substrate as described hereinabove.

The display rack for kits described herein may be adapted to retain the saliva test members in a manner permitting visual inspection of the absorbent material of the test members. In certain embodiments, the kits described herein comprise an optional display rack. The display rack can have any architecture or structural features in order to enable the rack to permit visual inspection of the absorbent material of the saliva test members. In some embodiments, the display rack is capable of retaining one or more test members concurrently, permitting a subject or clinician to visually inspect multiple test members simultaneously. The display rack can comprise or be formed from any material. For example, a display rack can comprise or be formed from a plastic, or can comprise or be formed from cardboard or a reinforced paper product. In some embodiments, a container for the saliva test members may also be used as a display rack of a kit described herein. Persons having skill in the art will recognize and appreciate that devices may be provided and used alone, or multiple devices may be provided in a kit for comparison, where desired.

II. Methods of Using a Bodily Fluid Indicator Device

In a further aspect, methods of using a bodily fluid indicator device are provided. In some embodiments, a method includes providing a bodily fluid indicator device comprising a region of absorbent material and a graduated scale printed thereon. The graduated scale may be printed from a food grade or FDA approved ink that is water soluble.

In some embodiments, the method can further include contacting a bodily fluid with the indicator device for a period of time sufficient to cause the bodily fluid to migrate over a portion of the graduated scale. Notably, the period of time is less than two minutes. In some embodiments, the period of time is approximately one minute or less, approximately 45 seconds or less, between about 30 seconds and two minutes, or a subrange thereof (e.g., 30-45 seconds, 1-2 minutes, etc.). In further embodiments, the period of time is approximately 30 seconds or less.

In some embodiments, the method includes determining an increase or decrease regarding an amount of bodily fluid present based on a proportion of the graduated scale over which the bodily fluid has migrated. The change (i.e., increase or decrease in bodily fluid) may be observed on the amount of the graduated scale over which the bodily fluid has migrated. The subject may then undergo additional testing for diagnosing the cause of a deficient amount of fluid.

In other embodiments, where bodily fluid migrates over three or more portions (e.g., increments) of the graduated scale, the test may indicate that the amount of bodily fluid obtained from a subject is within a normal range. Thus, bodily fluid indicator devices herein can indicate whether a subject's bodily fluid is within a normal range, or a range outside of what is considered normal. What is considered "normal" may vary based on the type of bodily fluid being obtained or the location of the test. For example, increments on a graduated scale for measuring saliva may be appropriate if spaced approximately 5 mm apart whereas increments on a graduated scale for measuring vaginal fluid may be appropriate if spaced approximately 10 mm apart.

As persons having skill in the art will recognize and appreciate, the length, placement, and/or incremental measurements on the graduated scale may be increased (e.g., in length or spacing) or decreased depending on the area being sampled and/or bodily fluid being sampled. Different bodily fluids may be tested using different scales and/or increments. In some methods, determining whether an amount of bodily fluid being produced is normal or abnormal is indicated using a graduated scale. The overall length of the scale and/or the spacing between increments on the scale can be set to an appropriate value for the type of bodily fluid being obtained and/or the area from which the bodily fluid is being obtained.

In some embodiments, methods herein further comprise folding or bending a plurality of tabs disposed on the bodily fluid indicator device for preventing a portion of the device from contacting the bodily fluid. For example, one or more tabs may be folded or bent to provide a "stop" to prevent the entire testing device from being inserted within a subject or otherwise contacting the bodily fluid. In an exemplary embodiment, the tabs are configured to contact a subject's skin or lips to prevent a stem portion of the device from extending within the subject's mouth during a saliva test. Other tabs, for example, may prevent the device from over-extension within a subject's nose, or vagina. Methods herein can be used to test any bodily fluid not inconsistent with the objectives noted herein.

In some embodiments, the device may be devoid of a graduated scale and/or include a graduated scale and one or more other reactive, indicative features printed thereon. Such features may react to a certain attributes of the bodily fluid, for example, temperature, pH, Biomarker, or chemical composition of the bodily fluid. That is, in some embodiments, methods herein can further comprise indicating an absence or presence of a chemical constituent in a bodily fluid based on the reaction (e.g., changes in color, intensity, etc.) of the reactive features over which the bodily fluid has migrated.

For example, such reactive features may indicate the absence or presence of a chemical or elemental constituent (e.g., the presence or absence of iron, calcium, glucose, sucrose, etc.), the absence or presence of a hormone, or the absence of presence of any other chemical attribute that is not inconsistent with the objectives of the instant disclosure. The features may indicate the absence or presence of a chemical or hormone and/or indicate a temperature or pH by changing color, intensity, quantity, size, visibility, etc.

In some embodiments, visibility or non-visibility of one or more reactive features indicates the presence or absence of a chemical or elemental constituent in the bodily fluid. In an exemplary embodiment, a communication feature may be embedded on the device when specified compounds or Biomarkers are detected. Similarly, a feature may be visible on the device when estrogen is detected and invisible when estrogen is not detected. Test devices described herein may be printed with any suitable graduated scale and/or reactive feature for indicating various attributes (e.g., amount, specific elements present, specific compositional constituents present, temperature, pH, hormonal constituents, etc.) relating to a bodily fluid being tested.

In optional embodiments, the saliva test members (i.e., devices) may be weighed before and after insertion into the subject's mouth to obtain an initial weight and a final weight. A first test value can correspond to a weight of saliva present in or on a first saliva test member after use. To obtain a quantitative measurement of salivary production or flow, the first test value can be compared to provide a numerical difference between it and subsequent test values. In certain instances, the first test value can itself be used as a quantitative diagnostic measurement, such as by comparing the first test value to a "standard" value or range of values corresponding to normal, healthy, abnormal, or unhealthy levels of salivary production or flow. Other methods of quantitative measurement or comparison are also possible. For example, one or more of the saliva test members can comprise or include a capillary stem which provides a measurable distance that the saliva travels along the absorbent material in order to obtain a relative quantity of saliva collected on the first saliva test member. This would then be compared to a standard device, which provides a measurable value for comparison and quantification.

Some embodiments described herein are further illustrated in the following non-limiting examples.

Example 1

Figure 1A:
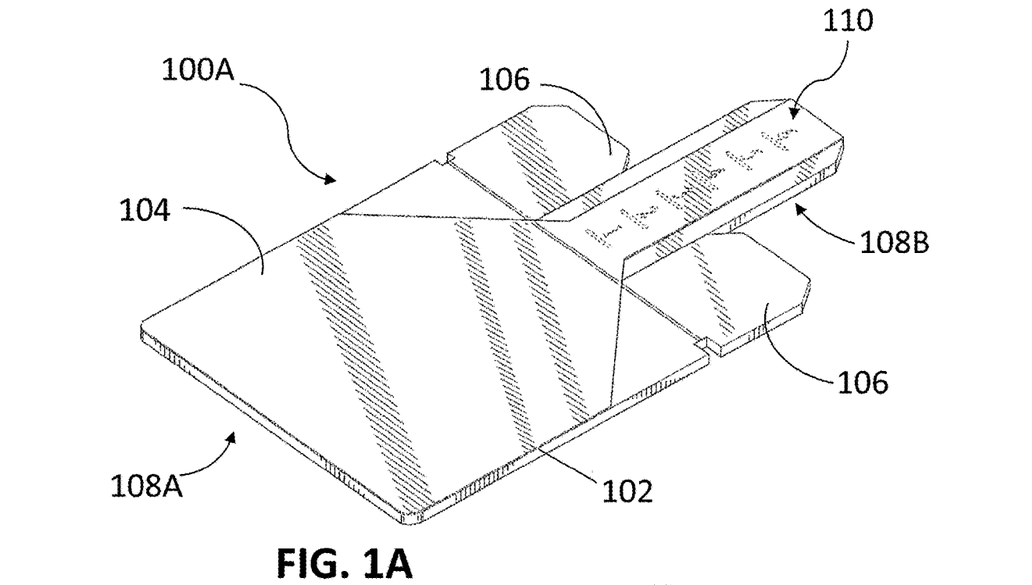
FIGS. 1A-1F are various views of a bodily fluid indicator device according to some embodiments.
Figure 1B:
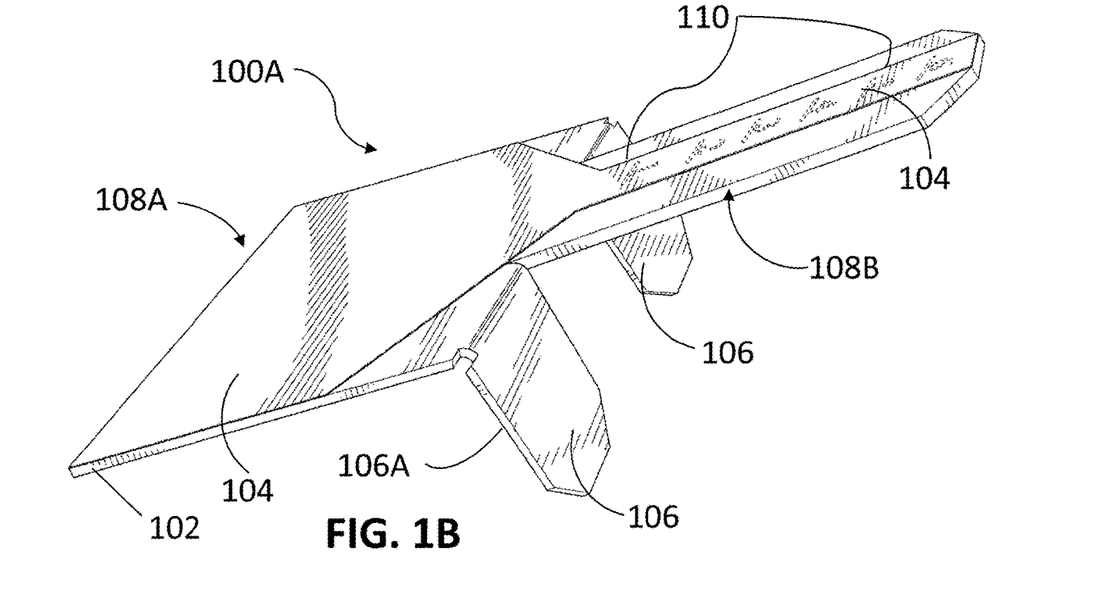

Devices and methods herein are configured to indicate at least an amount and/or a composition a bodily fluid present on an area of a subject or patient. FIGS. 1A and 1B illustrate bodily fluid indicator devices generally designated 100A.

As FIGS. 1A and 1B illustrate, device 100 can include a substrate 102 and an absorbent material 104 disposed on or over a portion of the substrate. Substrate 102 and/or absorbent material 104 can comprise semi-rigid or flexible, non-toxic materials suitable for placement on, over, or within a subject's body. In some embodiments, substrate 102 can comprise a body portion 108A and a stem portion 108B.

In some embodiments, absorbent material 104 comprises a paper, such as a porous filter paper over which a fluid migrates via capillary or osmotic phenomena. Absorbent material 104 is configured to face a mucus membrane or other body portion of a subject that emits or secretes bodily fluid. In an exemplary embodiment, absorbent material 104 is configured to face, contact, and then rest on a subject's tongue during a test. Saliva from the dorsal surface of the tongue contains saliva from all over the mouth (i.e., not just the floor of the mouth where the more powerful salivary glands are located). That is, device 100A is configured to test saliva secreted from multiple salivary glands, including the parotid gland.

Substrate 102 can comprise one or more flexible, creased, or otherwise bendable tabs 106 that can be folded or bent (FIG. 1B) for placement against a subject's skin. In some embodiments, tabs 106 are configured to rest or "stop" against a subject's skin for preventing portions of the device from becoming inserted within the subject's body. For example, in an exemplary embodiment a rear portion 106A of each tab 106 is configured to rest against a subject's lips, while absorbent material 104 disposed on body portion 108A of the substrate 102 rests over the subject's tongue for preventing stem 108B from entering the subject's mouth during the test. During the test, bodily fluid will migrate over a graduated scale 110 printed on device 100A. Graduated scale 110 is shown in broken lines as it is optional and/or may vary in size and/or increments, where desired. Device 100 takes advantage of a natural reflex of the tongue to push saliva to the front of the palate when the mouth closes, thus, saliva can be collected from glands above the tongue and below the tongue for ensuring a more thorough test.

In some embodiments, body portion 108A is at least 0.5 inches wide. In further embodiments, body portion 108A is approximately 1.5 inches wide. In some embodiments, body portion 108A can comprise a width ranging between approximately 0.5-2.5 inches.

In some embodiments, stem portion 108B is at least 0.125 inches wide. In further embodiments, stem portion 108B is approximately 0.25 inches wide. In further embodiments, stem portion 108B is approximately 0.5 inches wide. In some embodiments, stem portion 108B can comprise a width ranging between approximately 0.125-0.75 inches. Stem portion 108A can comprise a length of at least 1 inch or more, 2 inches or more, or a length ranging between approximately 0.5-12 inches.

Figure 1C:
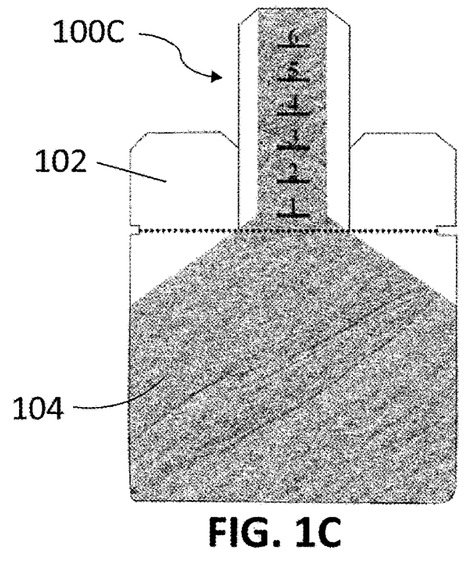
Figure 1D:
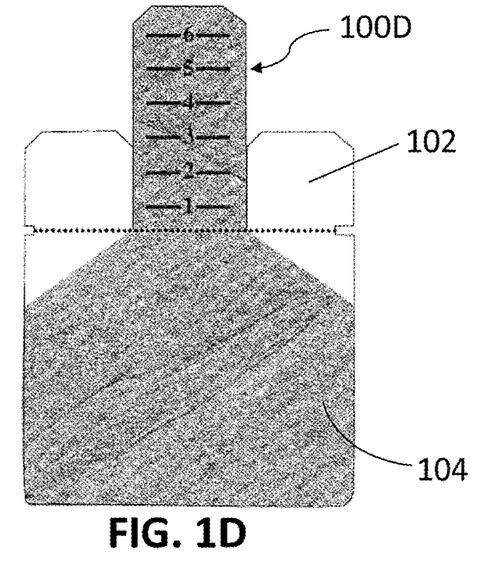
Figure 1E:
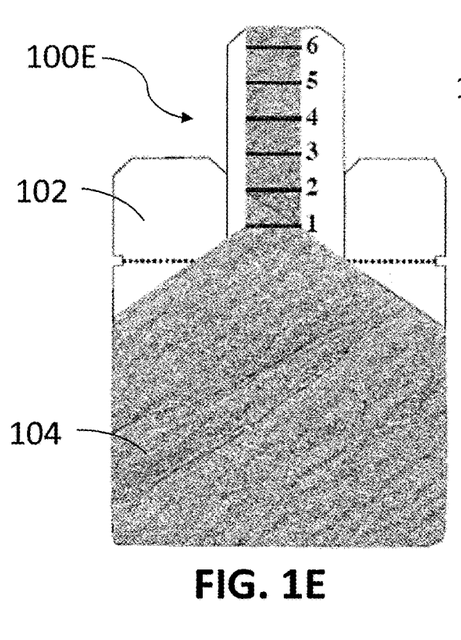

FIGS. 1C-1E illustrate further embodiments of bodily fluid indicator devices, generally designated 100C to 100E, respectively. Each device 100C to 100E can vary regarding the size, shape, and/or placement of graduated scale 110 and/or the size, shape, and/or placement of absorbent material 104. Such embodiments are shown for illustration purposes only. Persons having skill in the art will recognize and appreciate that devices may look a little different in regards to the sizes, shapes, and/or placement of various features.

Figure 1F:
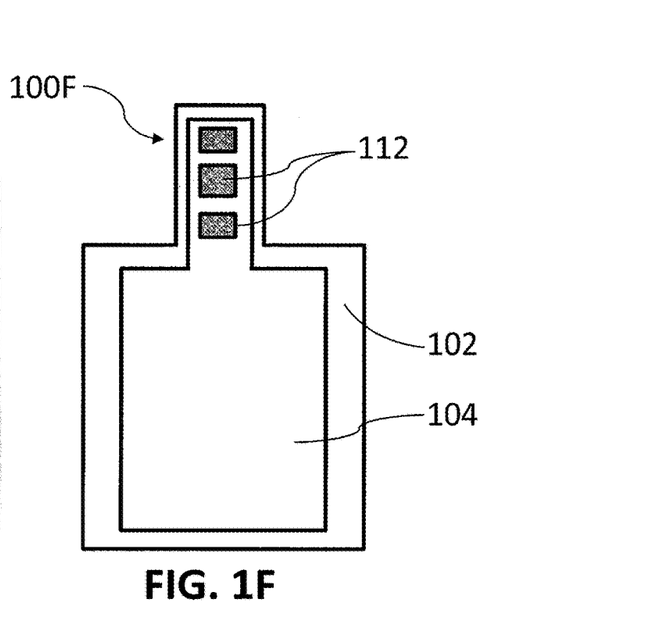

FIG. 1F is an exemplary embodiment of a bodily fluid indicator device 100F that is devoid of a graduated scale. However, FIG. 1F illustrates one or more reactive features 112 printed thereon. Such features 112 may be reactive (e.g., change in color, size, shape, intensity, etc.) to various chemicals, elements, hormones, bacteria, yeast, fluid temperature, fluid pH, etc., for indicating the absence or presence of a chemical or elemental constituent and/or a chemical composition forming the bodily fluid. Features 112 can indicate any number of chemical or physical attributes regarding the bodily fluid that migrates across the features.

For example, features 112 may react (e.g., change in size, shape, color, intensity, visibility, etc.) to calcium for indicating an amount of calcium present in the bodily fluid. In a further exemplary embodiment, features 112 may target and react to a specific hormone for indicating the presence or absence of the hormone in the bodily fluid.

Notably, devices described herein may include a graduated scale (e.g., 110), reactive features (e.g., 112), or a combination of both for indicating whether the type and/or amount of bodily fluid being produced is within a measurable range. As bodily fluid migrates over the graduated scale 110 and/or features 112, various attributes (e.g., chemical attributes, temperature, pH, volume, amount, production, gland viability, etc.) are indicated and become apparent.

Example 2

Figure 2A:
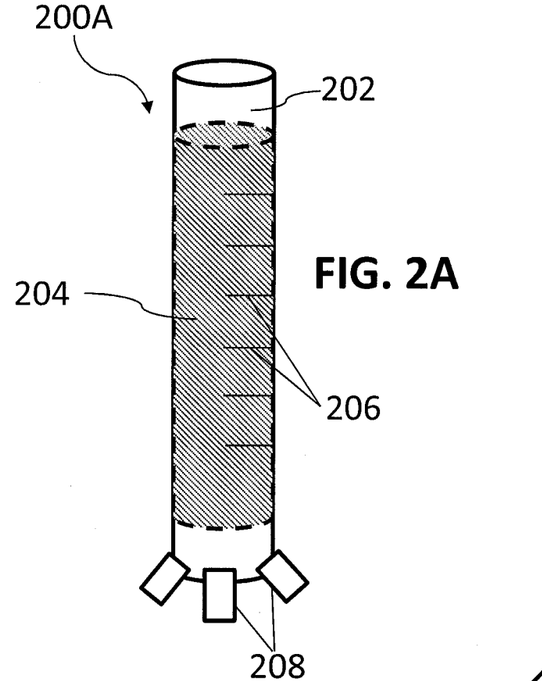
FIGS. 2A-2B are schematic views of various bodily fluid indicator devices according to some embodiments.
Figure 2B:
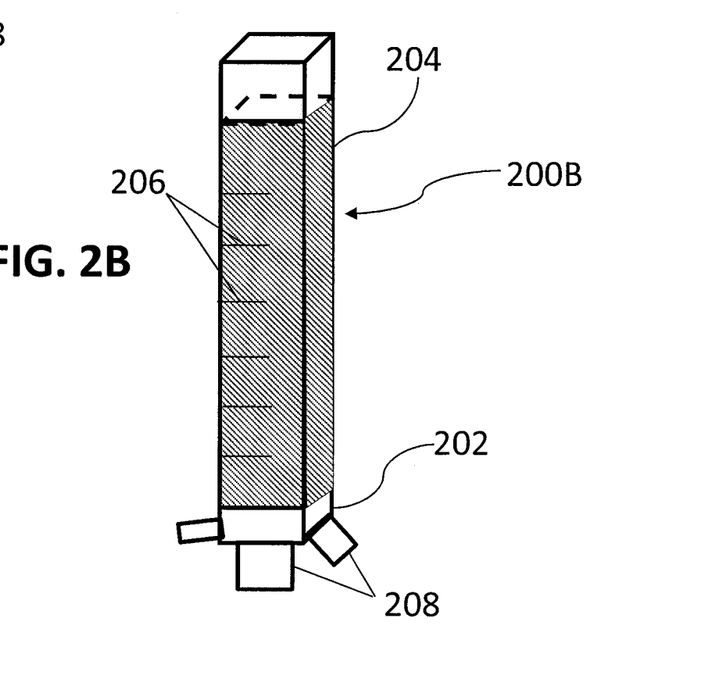

FIGS. 2A-2B are various schematic illustrations of bodily fluid indicator devices generally designated 200A-200B, respectively. FIG. 2A is a device 200A comprising a curved or rounded multidimensional substrate 202 and a correspondingly shaped region or area of absorbent material 204. Increments 206 forming a graduated scale are provided (e.g., printed) over the absorbent material. A plurality of tabs 208 can be disposed at one end for preventing the entire device from extending within a cavity of a subject's body. For example and in some embodiments, the tabs 208 may prevent the device from fully extending within a subject's nasal passage or vagina. Substrate 202 may be solid or hollow, where desired.

FIG. 2B is device 200B comprising an angular, multidimensional substrate 202 and a correspondingly shaped region or area of absorbent material 204. Increments 206 forming a graduated scale are provided (e.g., printed) over the absorbent material. A plurality of tabs 208 can be disposed at one end of device 200B for preventing the device from extending within a cavity of a subject's body.

Example 3

Figure 3:
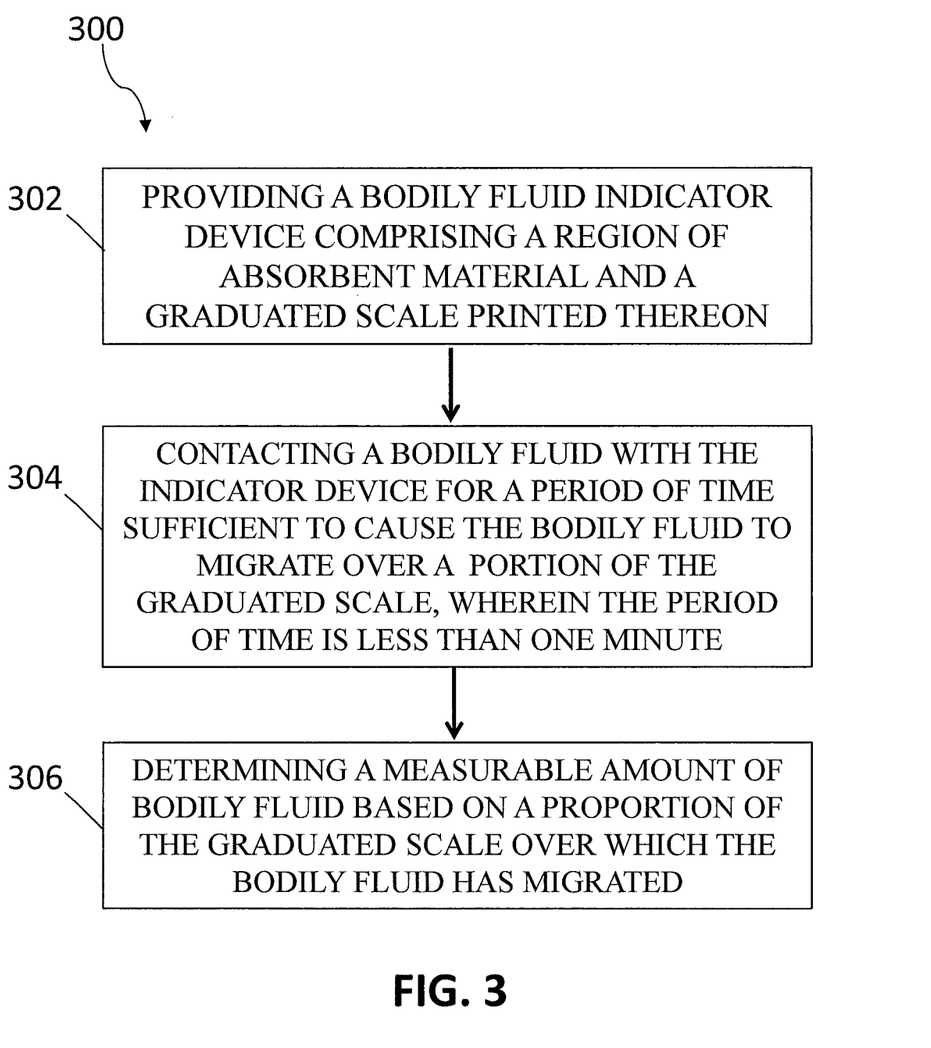
FIG. 3 is a flow chart of an exemplary method for using a bodily fluid indicator device according to some embodiments.

FIG. 3 is an exemplary embodiment of a method, generally designated 300, of using a bodily fluid indicator device to indicate an amount and/or composition of a bodily fluid. In block 302, a bodily fluid indicator device is provided. The device comprises a region of absorbent material and a graduated scale printed thereon. The graduated scale may be printed using a water soluble food grade ink. In lieu of and/or in addition to a graduated scale, one or more other features or shapes may also be printed on the absorbent material (see e.g., FIG. 1F). The features may indicate the absence or presence of a chemical or elemental constituent and/or a component of the bodily fluid.

In block 304, the device contacts a bodily fluid for a period of time sufficient to cause the bodily fluid to migrate over a portion of the graduated scale. Notably, the period of time can be less than two minutes or less than one minute.

In block 306, the measurable amount of bodily fluid is determined based on a proportion of the graduated scale over which the bodily fluid has migrated.

In another exemplary embodiment, a method of using a bodily fluid indicator device is provided. The method includes providing a bodily fluid indicator device comprising a region of absorbent material and one or more features printed thereon.

The method can further comprise contacting a bodily fluid with the indicator device for a period of time sufficient to cause the bodily fluid to migrate over a portion of the one or more features, wherein the period of time is less than one minute.

The method can further comprise indicating an absence or presence of a chemical constituent forming the bodily fluid based on a property or attribute regarding the one or more features over which the bodily fluid has migrated. For example, the features may indicate the absence or presence of a chemical or elemental constituent (e.g., the presence or absence of iron, calcium, glucose, sucrose, etc.), the absence or presence of a hormone, or the absence of presence of any other chemical attribute that is not inconsistent with the objectives of the instant disclosure. The one or more properties or attribute may include a color, intensity, or size of the one or more features for indicating the presence or absence of a chemical or elemental constituent in the bodily fluid.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention. In addition, one or more embodiments are illustrated by the figures filed concurrent herewith.

What is claimed is:

1. A bodily fluid indicator device, the device comprising:
a curved substrate;
a region of absorbent material covering portions of the substrate; and
a plurality of bendable tabs extending from the substrate;
wherein the tabs are movable between a first position being coplanar with the substrate and a second position being non-coplanar with the substrate;
wherein a proximal end of the absorbent material is configured to contact a source of bodily fluid so that bodily fluid migrates towards a distal end of the absorbent material, the distal end comprising a graduated scale or a reactive feature printed thereon,
wherein the tabs extend from a location of the substrate that is between the proximal end of the absorbent material and the distal end of the absorbent material, and
wherein the tabs, when in the second position, are configured to prevent the distal end of the absorbent material from contacting the source of the bodily fluid during collection of the bodily fluid.

2. The device of claim 1, wherein the substrate is flexible.

3. The device of claim 1, wherein the substrate comprises an organic material.

4. The device of claim 1, wherein the substrate comprises paper.

5. The device of claim 1, wherein the graduated scale is printed with a U.S. Food and Drug Agency (FDA) approved ink.

6. The device of claim 5, wherein the substrate comprises a capillary stem over which the bodily fluid travels a distance, the distance being visible and measurable.

7. The device of claim 1, wherein the substrate comprises a body portion and a stem portion extending from the body portion.

8. The device of claim 7, wherein the body portion is at least 0.5 inches wide.

9. The device of claim 7, wherein the stem portion is at least 0.125 inches wide.

10. The device of claim 7, wherein the body portion is wider than the stem portion such that the body portion is positionable over the source of the bodily fluid.

11. The device of claim 1, wherein the device is configured to indicate an amount and/or a composition of the bodily fluid present.

12. The device of claim 11, wherein the bodily fluid comprises saliva, nasal fluid, or vaginal fluid.

13. The device of claim 1, wherein the substrate is three-dimensional.

* * * * *